US009869607B2

(12) United States Patent
Mandal et al.

(10) Patent No.: US 9,869,607 B2
(45) Date of Patent: Jan. 16, 2018

(54) SYSTEMS AND METHODS FOR DISTRIBUTED MEASUREMENT

(71) Applicant: General Electric Company, Schenectady, NY (US)

(72) Inventors: Sudeep Mandal, Niskayuna, NY (US); Susanne Madeline Lee, Cohoes, NY (US); Sachin Narahari Dekate, Niskayuna, NY (US); Majid Nayeri, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 15/134,668

(22) Filed: Apr. 21, 2016

(65) Prior Publication Data

US 2017/0307471 A1   Oct. 26, 2017

(51) Int. Cl.
 G01N 21/00      (2006.01)
 G01M 11/00      (2006.01)
 G01J 5/48       (2006.01)

(52) U.S. Cl.
 CPC .......... G01M 11/319 (2013.01); G01N 21/00 (2013.01); G01J 5/48 (2013.01)

(58) Field of Classification Search
 CPC .......... G01M 11/319; G01J 5/48; G01K 11/00
 See application file for complete search history.

(56) References Cited

U.S. PATENT DOCUMENTS

| 6,817,759 | B2 | 11/2004 | Chi et al. |
| 7,245,790 | B2 | 7/2007 | Brown et al. |
| 7,719,666 | B2 | 5/2010 | Kishida et al. |
| 8,380,021 | B2 | 2/2013 | Kreisler Rambow |
| 8,630,816 | B2 | 1/2014 | Park et al. |
| 8,897,608 | B2 | 11/2014 | Kalar et al. |
| 2003/0103552 | A1* | 6/2003 | Chi .......... G01K 11/32 374/137 |
| 2012/0105826 | A1* | 5/2012 | Kalar .......... G01D 5/353 356/43 |

FOREIGN PATENT DOCUMENTS

CN          202002750 U      10/2011

OTHER PUBLICATIONS

Liu Yuan et al., "Application of Distributed Optical Fiber Temperature Sensing System Based on Raman Scattering in Coal Mine Safety Monitoring", Photonics and Optoelectronics (SOPO), 2012 Symposium on, pp. 1-4, May 21-23, 2012, Shanghai.

Miao Sun et al., "Study on spatial resolution improvement of distributed temperature sensor system by linear fitting algorithm", Proc. SPIE 9679, AOPC 2015: Optical Fiber Sensors and Applications, vol. 9679, Oct. 8, 2015, Beijing, China.

* cited by examiner

Primary Examiner — Jamil Ahmed
(74) Attorney, Agent, or Firm — Nitin N. Joshi

(57) ABSTRACT

A measurement system includes a cable having a length, a light source, at least one detector, and at least one processor. The light source is operably coupled to the cable and is configured to transmit an optical signal to the cable. The at least one processor is operably coupled to the cable and configured to: receive a scattered signal from the cable responsive to the optical signal transmitted to the cable; map the scattered signal to the length of the cable; and deconvolve a spatial averaging effect of the scattered signal using a weighting profile corresponding to the light source and the cable to generate a distributed property profile defined along the length of the cable.

23 Claims, 6 Drawing Sheets

SYSTEMS AND METHODS FOR DISTRIBUTED MEASUREMENT

BACKGROUND

Various approaches have been developed for measuring distributed properties of a given location, such as temperature or pressure. However, conventional techniques may not provide a desired resolution or accuracy.

Distributed temperature systems (DTS), for example, may employ a pulse of light sent down a fiber. A portion of the scattered light from the fiber is analyzed to determine temperature of the fiber. Conventional optical time-domain reflectometry (OTDR) DTS systems are generally limited in their spatial resolution by the width of the light pulse they generate to interrogate a fiber, and associated spreading of the light pulse. Current state of the art may provide about 50 centimeters of spatial resolution; however, in many applications it may be desired to resolve temperatures to smaller spatial resolutions. Potentially, smaller resolutions may be achieved by using shorter light pulses. However, use of shorter light pulses would result in a required tradeoff between shorter light pulses and the amount of scattered signal received back from the fiber. Furthermore, ultra-fast paced laser sources that are required for generating shorter light pulses are cost prohibitive for almost all applications.

BRIEF DESCRIPTION

In one embodiment, a measurement system is provided that includes a cable having a length, a light source, at least one detector, and at least one processor. The light source is operably coupled to the cable and is configured to transmit an optical signal to the cable. The at least one processor is operably coupled to the cable and configured to: receive a scattered signal from the cable responsive to the optical signal transmitted to the cable; map the scattered signal to the length of the cable; and de-convolve a spatial averaging effect of the scattered signal using a weighting profile corresponding to the light source and the cable to generate a distributed property profile defined along the length of the cable.

In another embodiment, a method is provided that includes transmitting, with a light source operably coupled to a cable, an optical signal to the cable. The method also includes receiving, with at least one processor operably coupled to the cable, a scattered signal from the cable responsive to the optical signal transmitted to the cable. Further, the method includes mapping the scattered signal to the length of the cable. Also, the method includes generating a distributed property profile defined along the length of the cable by de-convolving a spatial averaging effect of the scattered signal using a weighting profile corresponding to the light source and the cable.

In another embodiment, a tangible and non-transitory computer readable medium is provided that includes one or more computer software modules configured to direct one or more processors to: transmit an optical signal to the cable; receive a scattered signal from the cable responsive to the optical signal transmitted to the cable; map the scattered signal to the length of the cable; and generate a distributed property profile defined along the length of the cable by de-convolving a spatial averaging effect of the scattered signal using a weighting profile corresponding to the light source and the cable.

DETAILED DESCRIPTION

Figure 1:
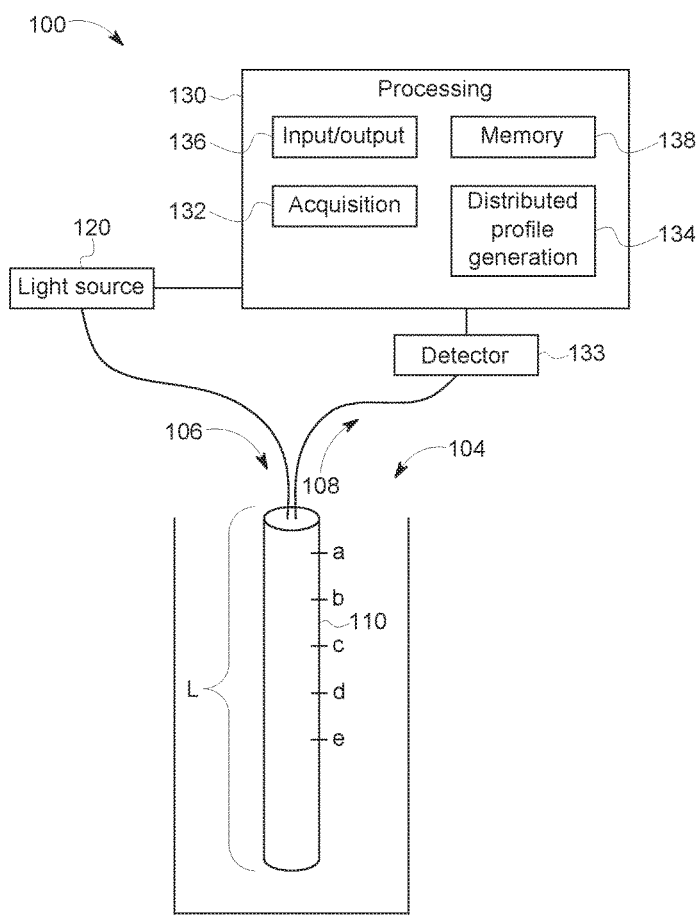
FIG. 1 is a schematic block diagram of a measurement system in accordance with various embodiments.

Various embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, any programs may be stand-alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. The modules or units shown in the attached figures may represent the hardware that operates based on software or hardwired instructions, the software that directs hardware to perform the operations, or a combination thereof. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Generally, various embodiments provide for distributed property determination along the length of a cable. Property distributions may be determined, for example, but without limitation, for strain, temperature, pressure, or acoustic properties. Various embodiments disclosed herein use oversampling (e.g., acquiring information at an interval less than an interval corresponding to a length of time of a transmitted pulse of light as received) of the returned light from a cable, along with knowledge of the shape of the pulse of light, to reconstruct a distributed property profile to spatial resolutions smaller than that of the light pulse.

For example, a conventional Raman based DTS yields spatially averaged data due to the fine spread of the interrogation light pulse within the optical fiber. Despite higher resolution sampling in time, the spread of the interrogating light pulse still results in approximately 50 centimeters spatial resolution with state of the art DTS systems. Various embodiments discussed herein de-convolve the effect of spatial averaging, yielding substantial improvement to resolution (e.g., resolution of 20 centimeters or less in various embodiments) without requiring changes or upgrades to sensing system hardware.

Generally, in various embodiments, a weighting function is constructed to describe the spatial averaging profile of the probing light pulse. For example, the weighting function may be determined by subjecting an optical fiber to known temperature profiles. The weighting function or profile is invariant for a given optical fiber/sensing system combination so the weighting function may be characterized only once, for example as part of a calibration process. Once the spatial profile is determined, it may be used to de-convolve higher resolution data and recover higher spatial resolution measurements from a distributed time domain fiber optic sensing system. It may be noted that, in some embodiments, the weighting function varies along the length of the cable. For example, in some embodiments the weighting function becomes broader further along a fiber or cable (e.g., at increasing distances from the light source) to account for dispersion in the fiber. The amount of broadening appropriate to address the dispersion may be determined during a calibration procedure.

At least one technical effect of various embodiments is providing for improved spatial resolution capabilities of time domain fiber optic sensing systems. At least one technical effect of various embodiments is improved resolution without requiring increases in system cost. At least one technical effect of various embodiments is improved convenience and/or accuracy for distributed property readings, such as strain, pressure, or temperature along the length of a cable.

FIG. 1 is a schematic view of a measurement system 100 formed in accordance with various embodiments. The measurement system 100 is configured to measure one or more environmental conditions or properties of a remote location 104 and generate a distributed property profile describing one or more properties at various points within the remote location 104. For example, the measurement system 100 may measure a temperature, a pressure, or a strain at various points of the remote location 104. As another example, the measurement system 100 may measure acoustic properties. The remote location 104 depicted in FIG. 1 is shown as having a generally vertical configuration for clarity and ease of illustration; however, for example, in various embodiments, the remote location may also have horizontally oriented portions or volumes but not limited to any geometry. The remote location 104 may be understood as being remote in that the remote location 104 is located at a distance from components of the measurement system 100 configured to generate and/or receive a signal from sensing equipment disposed within the remote location 104. Thus, signal generation and/or signal processing equipment, for example, may be maintained under different environmental conditions than the remote location 104.

The measurement system 100 depicted in FIG. 1 includes a cable 110, a light source 120, a detector 133, and a processing unit 130. It may be noted that the depicted detector 133 may represent one or more detectors (e.g., photodetectors) and/or associated components or circuitry, including detectors, filters, amplifiers, and/or various optoelectronic circuits to convert light signals to representative electrical signals. The light source 120 and processing unit 130 are operably connected to the cable 110. Generally, in various embodiments, the light source 120 is configured to generate an optical signal 106, or pulse, that is transmitted to the pressure sensing cable 110. The optical signal 106, for example, may be an optical signal including light at a particular wavelength or across a bandwidth of wavelengths. The cable 110 in various embodiments includes an optic fiber that receives the optical signal 106. The optical signal 106 is transmitted through the cable 110, with a return signal 108 generated within the cable 110 responsive to the optical signal 106. The return signal 108 in the illustrated embodiment is a backscattered signal including backscattered light generated as the optical signal 106 propagates along a length L through the cable 100. The cable 110 is configured so that the return signal 108 includes portions associated with various lengths (e.g., depths in a vertical application) distributed along a length L of the cable 110. For example, a portion of the return signal 108 corresponding to backscatter at point a along length L is received before a portion of the return signal 108 corresponding to backscatter at point b along length L, which is returned before a portion of the return signal 108 corresponding to backscatter at point c along length L, and so on. In the illustrated embodiment, the detector 133 receives scattered light (e.g., backscattered light), and generates electrical signals used by the processing unit 130. The processing unit 130 is configured to obtain (e.g., receive) the return signal 108 (e.g., via the detector 133), and to map the backscattered signal (or portion thereof) to the length L of the cable. As used herein, receiving the backscattered signal (or other scattered signal) may include reception of the scattered light and/or reception of electrical signals corresponding to scattered light. For example, the detector 133 may receive scattered light and produce an output signal corresponding to the scattered light that is received by the processing unit 130.

By knowing the speed of light and time of transmission of the optical signal 106, as well as time of reception of a given portion of the return signal, the given portion of the return signal may be identified with a particular position along the length, with portions of signals corresponding to portions of the cable 110 nearer the light source 120 received before portions of signal corresponding to portions of the cable 110 farther from the light source 120. Further, the mapping of the backscattered signal to the length L of the cable may include mapping an original or raw property profile determined using the backscattered signal to the length L of the cable.

It may be noted that the optical signal 106 traveling along the cable 110 is not concentrated at a single discrete point, but instead has a length corresponding to the pulse rate. With the speed of light being quite high, even a relatively fast pulse rate may produce a pulse having a length between 0.5 and 1 meter for light sources available for practical use at reasonable prices. A relatively short pulse duration produces a relatively short length of pulse, while a longer pulse duration produces a longer length of pulse. The longer the length of the pulse, the more limited will be the resolution of the measurement system 100. The length of the pulse results in a spatial averaging effect that may limit or reduce spatial resolution if not addressed. Accordingly, in the illustrated embodiment, the processing unit 130 is also configured to de-convolve a spatial averaging effect of the backscattered signal (return signal 108) using a weighting profile to generate a distributed property profile defined along the length of the cable (e.g., a first value of the property for point a, a second value of the property for point b, a third value of the property for point c, and so on). The weighting profile corresponds to the light source 120 and the cable 110. The combination of light source and cable produces a particular pulse profile (e.g., intensity of pulse along the length of the pulse), which may vary if either the source or the cable are changed. Accordingly, the particular weighting profile employed may be defined by the combination of the source and the cable, with a different weighting profile used for each source/cable combination.

Due to the smearing or averaging effect of the length of pulse (e.g., a pulse duration faster than a sampling or acquisition rate), information from or corresponding to neighboring or nearby points along the length L of the cable 110 may be convolved with each other. For example, information corresponding to a given point (e.g., point c), may include information from other points (e.g., points b and d), and/or information regarding point c may be included with information sampled at a time corresponding to other points (e.g., points b and d). Whereas a conventional distributed measurement system may use only information sampled at a single point in time corresponding to a single point along a length, various embodiments disclose herein use information corresponding to a sequence of points including a given point (e.g., centered about a given point) to determine the property value at the given point.

In various embodiments, the light source 120 transmits the optical signal 106 at a pulse duration, and the processing unit 130 acquires the backscattered signal (return signal 108) at a sampling rate that is faster than the pulse duration. Because higher sampling rates may be more economically feasible or attainable for electronic systems, compared to optic systems, readily or reasonable obtainable acquisition system may have faster rates than readily or reasonably obtainable transmission systems (e.g., light source 120), resulting in "oversampling" relative to the pulse produced, with the resolution limited by the pulse length. However, various embodiments discussed herein address the averaging effect resulting from the length of the pulse to provide a spatial resolution approaching the resolution available from the sampling rate instead of being limited to the resolution corresponding to the pulse length.

Figure 2:
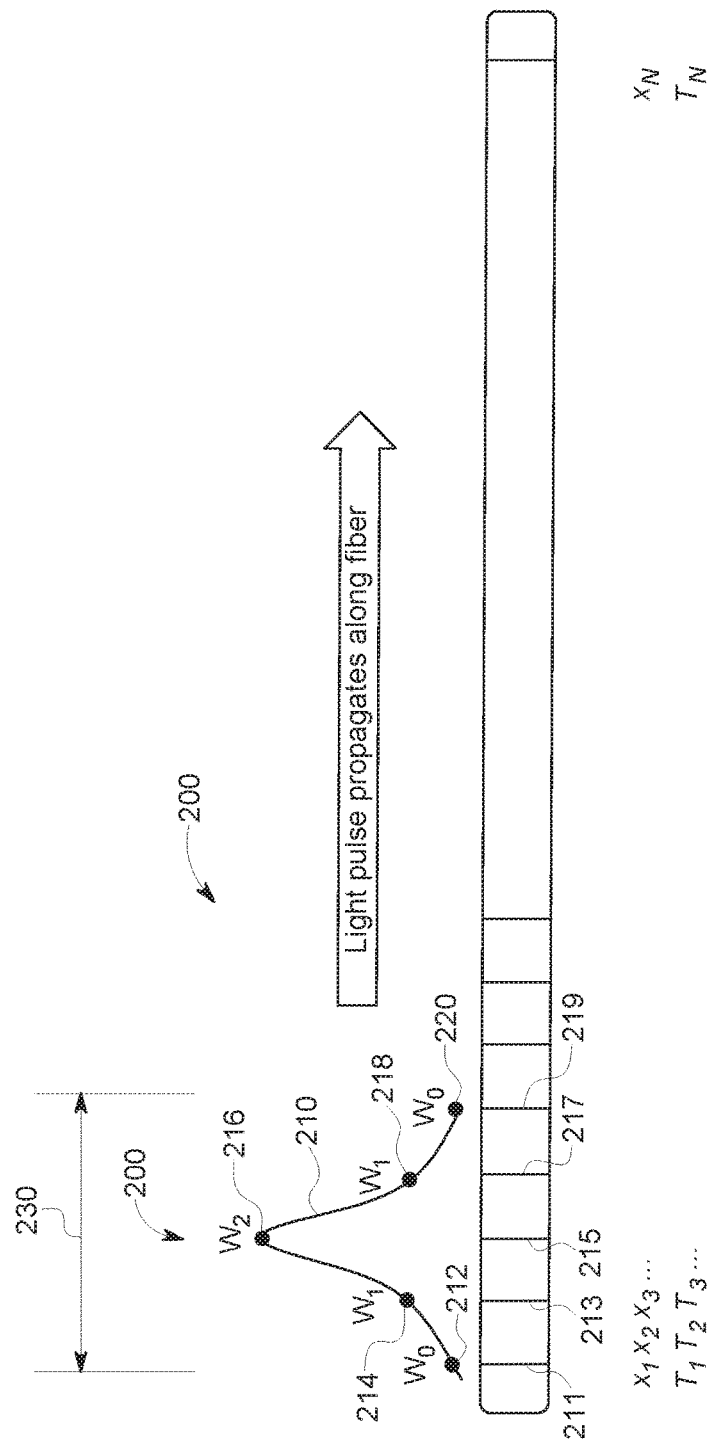
FIG. 2 illustrates an example depiction of a pulse having a weighting profile in accordance with various embodiments.

For example, the pulse duration may result in a pulse that is 50 centimeters long, and the sampling rate may provide information corresponding to every 12.5 centimeters along the length L. Accordingly, 5 different sampling points may be associated with the position of the 50 centimeter pulse at a given point in time. FIG. 2 illustrates an example depiction 200 of a pulse 202 having a weighting profile 210 as the pulse 202 propagates along a fiber 204. The backscattered signal may be sampled at times 211, 213, 215, 217, 219, corresponding to data points 212, 214, 216, 218, 220, respectively. The example weighting profile 212 is symmetric about a peak corresponding to data point 216, so that data points 212 and 220 may use the same weighting coefficient $w_0$, and data points 214 and 218 may also use a common weighting coefficient $w_1$. For example, in FIG. 2, the weighting profile 210 may correspond to a pulse length 230 of 50 centimeters with 12.5 centimeters between data points at which the backscattered signal is acquired at the sampling rate. It may be noted that the example of FIG. 2 is provided for clarity of illustration and is meant by way of example. Other shapes or values (such as pulse length and/or sampling rate) may be employed in various embodiments. For convenience, the sampling rate may be configured to provide information corresponding to an interval length that is at or near an integer fraction of the total length of the pulse resulting from the pulse duration.

Generally, with continued reference to the example of FIG. 2, the measured temperature may be understood as a convolution of the true temperature and light pulse weighting profile. This may be expressed for example, as $$T_{m_j} = \sum_{i=j-2}^{i=j+2} w_i T_i$$

where $T_m$ is the measured temperature, w is the light pulse weighting profile, and T is the true temperature. In this example, 5 data points (j−2, j−1, j, j+1, j+2) are used to define the temperature corresponding to a given point j. The relationship between the weighting, temperature T and measured temperature $T_m$ may also be expressed as $$\begin{bmatrix} w_0 & \cdots & w_L & 0 & \cdots & \cdots & \cdots & 0 \\ 0 & w_0 & \cdots & w_L & 0 & & & \vdots \\ \vdots & 0 & \ddots & \cdots & \ddots & 0 & & \vdots \\ \vdots & & 0 & \ddots & \cdots & \ddots & 0 & \vdots \\ \vdots & & & 0 & w_0 & \cdots & w_L & 0 \\ 0 & \cdots & \cdots & \cdots & 0 & w_0 & \cdots & w_L \end{bmatrix} \begin{bmatrix} T_1 \\ T_2 \\ \vdots \\ \vdots \\ T_N \end{bmatrix} = \begin{bmatrix} T_{m_1} \\ T_{m_2} \\ \vdots \\ \vdots \\ T_{m_M} \end{bmatrix}$$

Still another way to express the relationships is $W^*t=t_m$, where W is a weighting, t is the true temperature, and $t_m$ is a measured temperature. Generally, the measured temperature may be determined using the return signal 108. For example, to determine measured temperature, the return signal 108 may be analyzed using a conventional analysis, such as a Raman analysis of the return signal. However, as discussed herein, the measured temperature as determined may suffer from an averaging or spreading effect of the light pulse. Accordingly, a weighting W may be used. Once the weighting W is known, the above equations may be utilized (e.g., inverted numerically using a least squares technique) to solve for the true temperature t using the weighting W and the measured temperature $t_m$.

In some embodiments, a weighting profile ($w_0 \ldots w_L$) may be determined experimentally. For example, a known temperature profile may be applied to a cable using an experimental setup (e.g., placing known points along the cable within a liquid bath of a known temperature). Then weighting profile ($w_0 \ldots w_L$) candidates may be calculated using the known temperature profile of the bath and the measured temperature profile. In other embodiments, the weighting profile may be determined using calculations based on the properties of the light source and/or cable. As discussed herein, in some embodiments, the weighting function varies along the length of the cable. For example, in some embodiments the weighting function becomes broader further along a fiber or cable (e.g., at increasing distances from the light source) to account for dispersion in the fiber, with the amount of broadening appropriate to address the dispersion determined during a calibration procedure.

Figure 3:
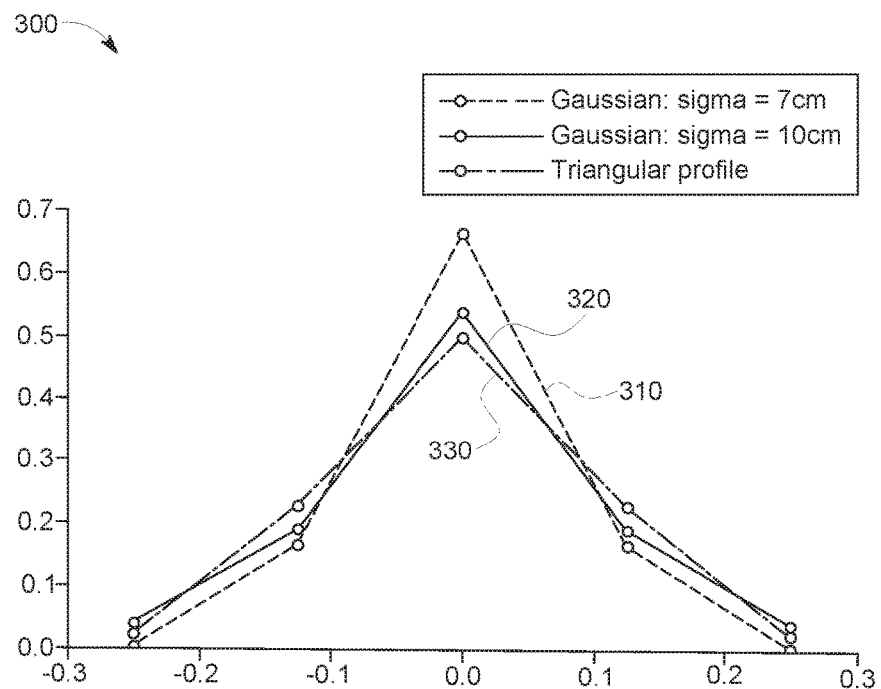
FIG. 3 illustrates example weighting profiles in accordance with various embodiments.

Different shapes of weighting profiles may be used in different embodiments. For example, in some embodiments, the weighting profile may have a Gaussian (or bell curve) shape. As another example, in some embodiments, the weighting profile may have a triangular shape. FIG. 3 illustrates example weighting profiles including 5 points each. Other profile shapes and/or other numbers of data points may be used in various alternate embodiments. Figure illustrates three different weighting profiles—a first Gaussian profile 310, a second Gaussian profile 320, and a triangular profile 330. As seen in FIG. 3, the first Gaussian profile 310 has a Sigma of 7 centimeters and the second Gaussian profile 320 has a Sigma of 10 centimeters. The first Gaussian profile 310 is generally steeper or more sloped toward its peak in the center than the second Gaussian profile. The triangular profile 330, which need not necessarily define a perfectly triangular shape in various embodiments, is flatter than the Gaussian profiles. The particular shape of weighting profile chosen may be selected, for example, based on experimental testing as discussed herein.

It may be noted that, in the example shown in FIG. 3, each profile is based on 5 points which correspond to the sampling rate. However, the use of more points may be employed to provide a profile that gives a shape more representative of a true Gaussian shape. For example, in some embodiments, temperature (or other property) profile resolution may be increased, using a higher resolution pulse weighting profile, such as a first order approximation of a Gaussian shaped light pulse. Also, a higher resolution cubic spline fit may be used for raw data (e.g., distributed temperature data) that is acquired at a lower resolution sampling rate. The acquired data may then be de-convolved using the weighting profile to recover a higher resolution reconstructed profile. In some embodiments, a priori physics based knowledge regarding light pulse weighting (e.g., physical properties of the cable and/or light source) may be used in determining or developing the weighting profile.

Figure 4:
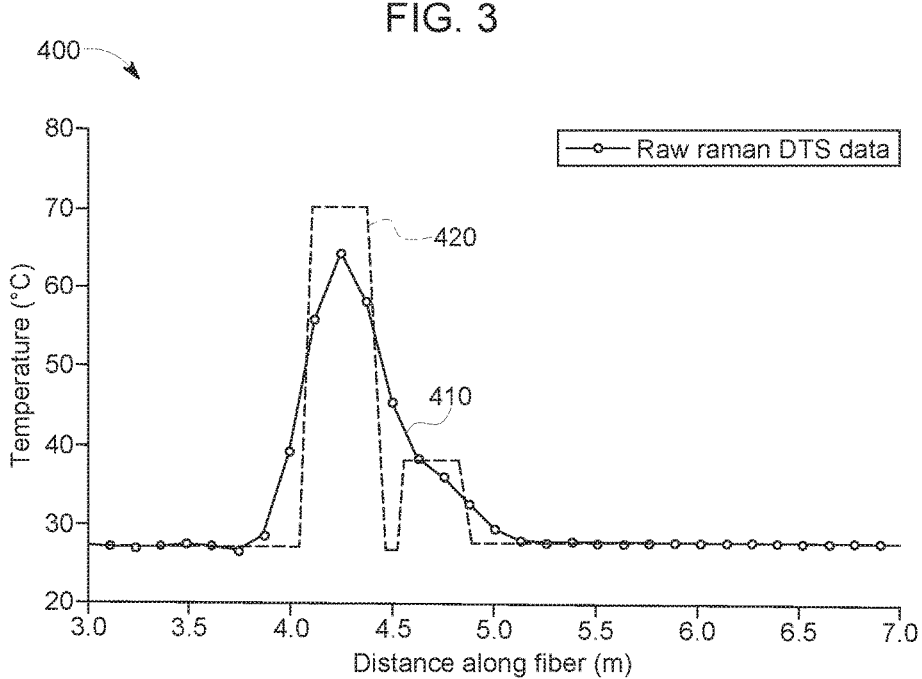
FIG. 4 provides a graph showing raw Raman distributed temperature data in accordance with various embodiments.
Figure 5:
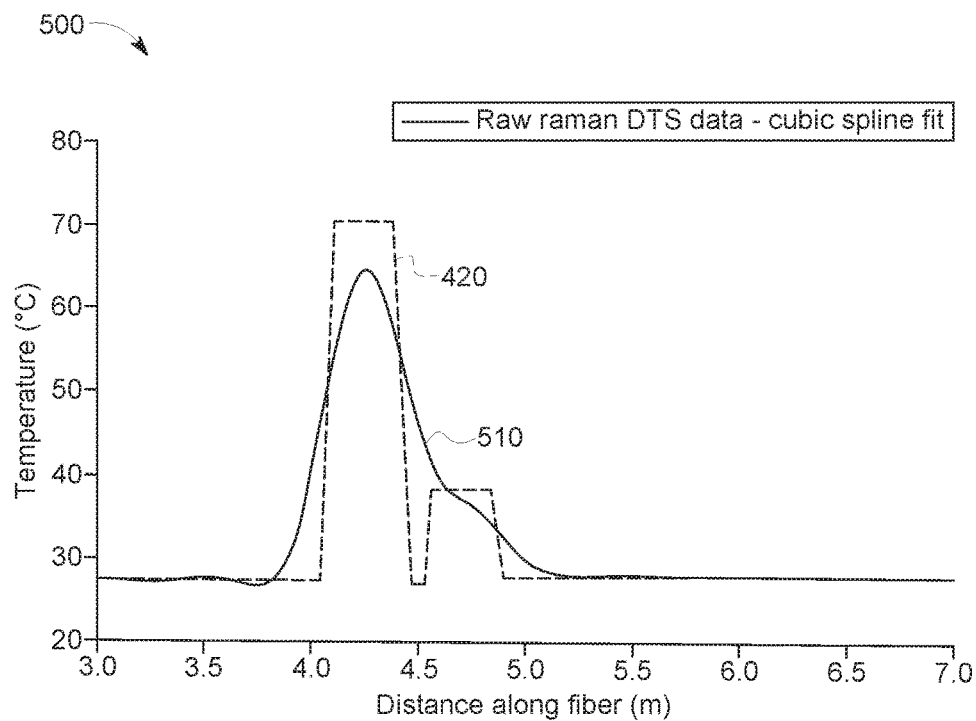
FIG. 5 is a graph of modified temperature data from FIG. 4.
Figure 6:
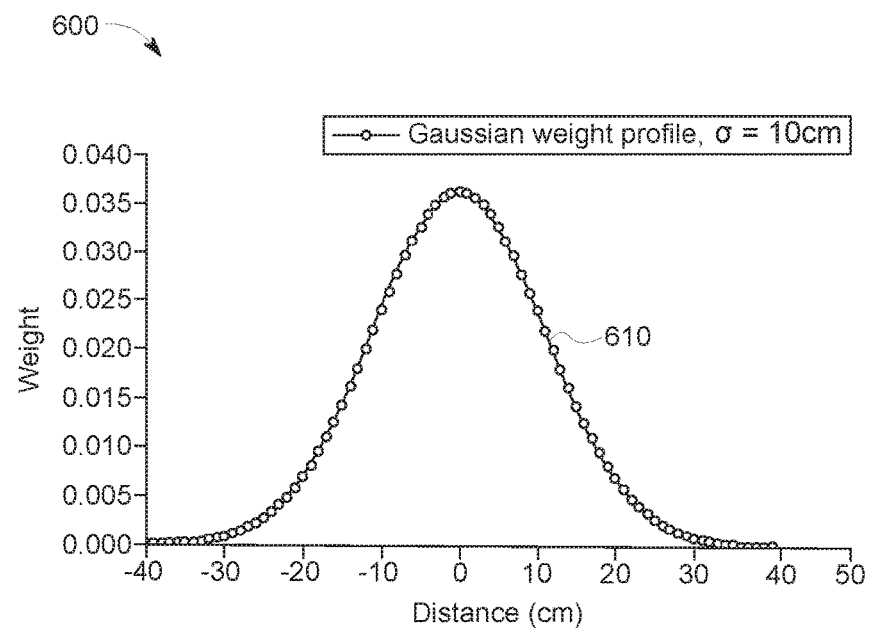
FIG. 6 is a graph of a Gaussian weight profile for use with the examples of FIGS. 4 and 5.
Figure 7:
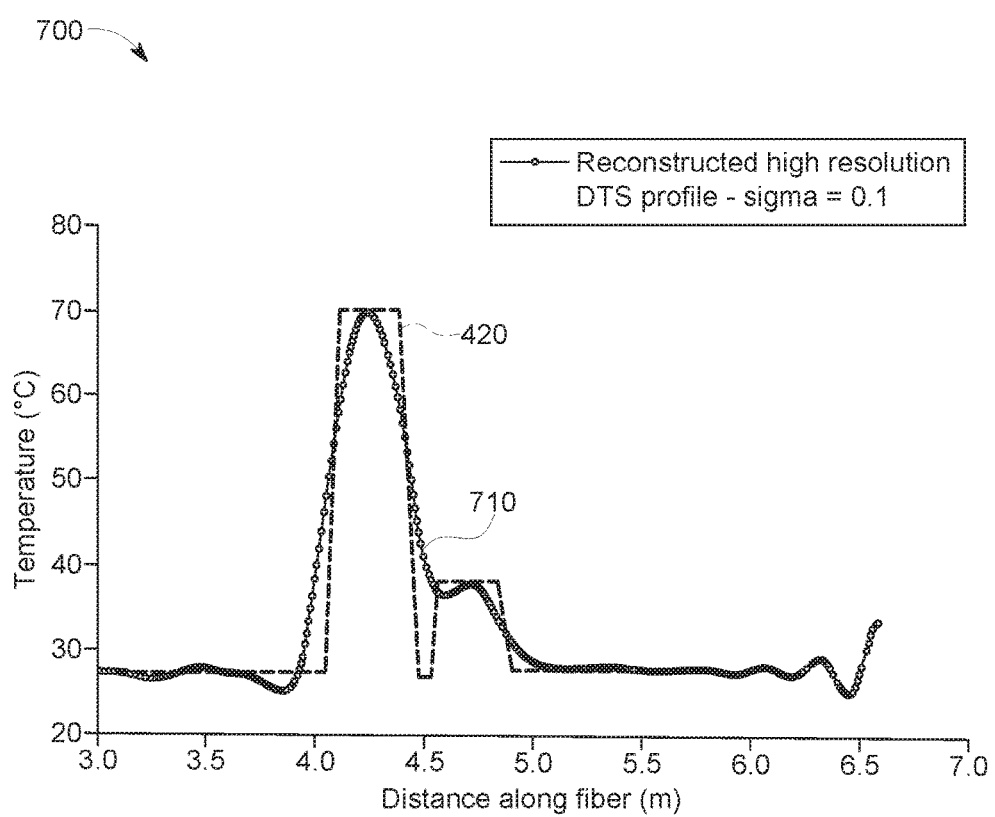
FIG. 7 is a graph of a temperature profile generated in accordance with various embodiments.

For example, FIG. 4 provides a graph 400 showing raw Raman distributed temperature data 410 acquired at a 12.5 centimeter sampling interval, plotted as temperature vs. distance along a fiber. A true temperature profile 420 is also shown in FIG. 4. To obtain the true temperature profile 420, different lengths of the fiber may be placed in baths of predetermined temperature (e.g., as seen in FIG. 4, a first length in a bath of about 70 degrees Celsius and a second length in a bath of about 37 degrees Celsius). FIG. 5 provides a graph 500 showing the true temperature profile along with modified temperature data 510. The modified temperature data 510 is generated by constructing a high-resolution cubic-spline fit of the raw Raman distributed temperature data 410. The high-resolution cubic-spline fit in the illustrated example has a sampling interval of 1 centimeter, compared with 12.5 centimeters for the raw data. FIG. 6 provides a graph 600 showing a Gaussian weight profile 610 corresponding to a 1 centimeter sampling interval (e.g., matching the cubic spline fit interval). The modified temperature data 510 may then be de-convolved using the high resolution Gaussian weight profile 610 to recover a high resolution temperature profile. FIG. 7 provides a graph 700 showing a recovered high resolution temperature profile 710, along with the true temperature profile 420. As seen in FIGS. 4 and 7, the high resolution temperature profile 710 is a better fit with the true temperature profile 420 and has higher resolution than the raw Raman distributed temperature data 410 that is obtainable using conventional techniques.

Returning to FIG. 1, it may be noted that different distributed properties (e.g., temperature, pressure, strain) may be measured or determined in various embodiments, and that various techniques may be used. Generally, various embodiments utilize a time domain analysis of backscattered light to determine a distributed property (e.g., a property having varying values along a length of fiber or cable). In some embodiments, the processing unit 130 is configured to generate a distributed temperature profile along the length L of the cable 110. For example, the processing unit 130 may analyze Raman scattering from the cable 110 to determine the distributed temperature profile.

As discussed herein, the optical signal 106, for example, may be an optical signal including light at a particular wavelength or across a bandwidth of wavelengths. It may be noted that, in some embodiments, the light source 120 transmits the optical signal at a pulse wavelength, and the processing unit 130 acquires and analyzes the backscattered signal at the pulse wavelength. For example, Rayleigh scattering may be analyzed in this fashion, and used to determine a distributed strain or acoustic properties. In other embodiments, the light source 120 transmits the optical signal at a pulse wavelength, and the processing unit 130 acquires and analyzes the backscattered signal at at least two wavelengths that are different from the pulse wavelength. For example, the processing unit 130 may acquire and analyze information at a first wavelength that is longer than the pulse wavelength (Stokes wavelength) and at a second wavelength that is shorter than the pulse wavelength (anti-Stokes wavelength). Raman scattering may be analyzed in this fashion, for example to determine a distributed temperature profile. Similarly, Brilloun scattering may be analyzed in this fashion, for example to determine a distributed temperature or strain profile. While the illustrated example is described using backscattering, it may be noted that other scattering (e.g., forward scattering) of light may be employed and analyzed in other embodiments. For example, ackscattering is one system architecture of Raman and Brillouin systems. However, such systems (or systems using an additional or alternative analysis technique) may be operated using a round trip architecture, for example with 2 light sources and 2 detectors and having access to both ends of the cable. Various techniques for increasing spatial resolution disclosed herein may apply regardless of which architecture or scattering is employed.

In the illustrated embodiment, the processing unit 130 is configured to receive a backscattered signal (e.g., return signal 108) generated in the cable 110 responsive to the optical signal (e.g., send signal 106) transmitted by the light source 120. The processing unit 130 is also configured to determine a measured distributed property (e.g., temperature) profile using the backscattered information (e.g., using a time domain analysis such as a Raman analysis, Brilloun analysis, or Rayleigh analysis). The processing unit 130 is further configured to de-convolve a spatial averaging effect of the backscattered information using a weighted profile to generate a distributed property profile as discussed herein, with improved resolution compared to the originally determined measured distributed property profile.

It may be noted that, in various embodiments, the weighting profile may be at a higher spatial resolution than a resolution determined or provided by the sampling rate (see, e.g., FIGS. 5-7 and related discussion), and the processing unit 130 interpolates a scattered signal to provide increased resolution for de-convolving the spatial averaging effect. Accordingly, improved spatial resolution of a recovered or generated distributed property profile is achieved. It may also be noted that, in various embodiments, the processing unit 130 is configured to control the light source 120 and the detector 133 to synchronize acquisition of the scattered signal via the detector 133 with transmission of the optical signal 106. Accordingly, timing jitter in a received signal may be reduced, which reduces noise. Such reduction of noise via reduced timing jitter provides higher fidelity deconvolution with improved spatial resolution of a recovered or generated distributed property profile.

In the illustrated embodiment, the processing unit includes an acquisition unit 132, a distributed profile generation unit 134, an input/display unit 136, and a memory 138. It may be noted that the particular units or modules shown in FIG. 1 are meant by way of example, and that other arrangements of units or sub-units of the processing unit 130 may be employed in various embodiments. Generally, the various aspects of the processing unit 130 act individually or cooperatively with other aspects to perform one or more aspects of the methods, steps, or processes discussed herein (e.g., method 800 or aspects thereof). Instructions to perform one or more aspects of the methods, steps, or processes discussed herein may be stored on the memory 138, which may include a tangible, non-transitory computer readable medium on which the instructions are saved. The processing unit 130 may also be configured to control operation of the light source 120.

Generally, in the illustrated embodiment, the acquisition unit 132 is configured to obtain (e.g., receive, acquire, or the like) information from the cable 110 (e.g., via the detector 133) disposed in the remote location 104. In various embodiments, the information may be provided via a return signal 108 including backscattered data from the cable 110 corresponding to reflections of the send signal 106 transmitted to the sensing cable 110 from the light source 120. The acquisition unit 132 may be configured to filter (e.g., remove noise, signals from wavelengths not of interest to processing, or the like) or otherwise process the received return signal 108 in various embodiments. In some embodiments, the acquisition unit 132 may be configured for use with a tunable laser.

In the illustrated embodiment, the distributed profile generation unit 134 is configured to use a weighting function corresponding to a light source and/or cable to de-convolve a spatial averaging effect and provide a distributed property (e.g., temperature, pressure, strain) profile with improved resolution. For example, the depicted distributed profile generation unit 134 obtains (e.g., receives, acquires, or the like) information (e.g., the return signal 108, or portions of the return signal 108, either processed or raw in various embodiments) from the acquisition unit 132, determines an original distribution profile, and de-convolves a spatial averaging effect from the original distribution profile using a weighting function to provide a distributed property profile.

In the example depicted in FIG. 1, the input/output unit 136 is configured to receive one or more inputs, for example, from a user, and to display information to a user, for example, a distributed property profile that has been generated by the processing unit 130. The input/output unit 136 may include one or more of a touchscreen, keyboard, mouse, keypad, or the like. The input/output unit 136 may also be configured to automatically or autonomously retrieve information regarding a weighting function or the like for a given cable/light source combination via a database accessible to the input/output unit.

Figure 8:
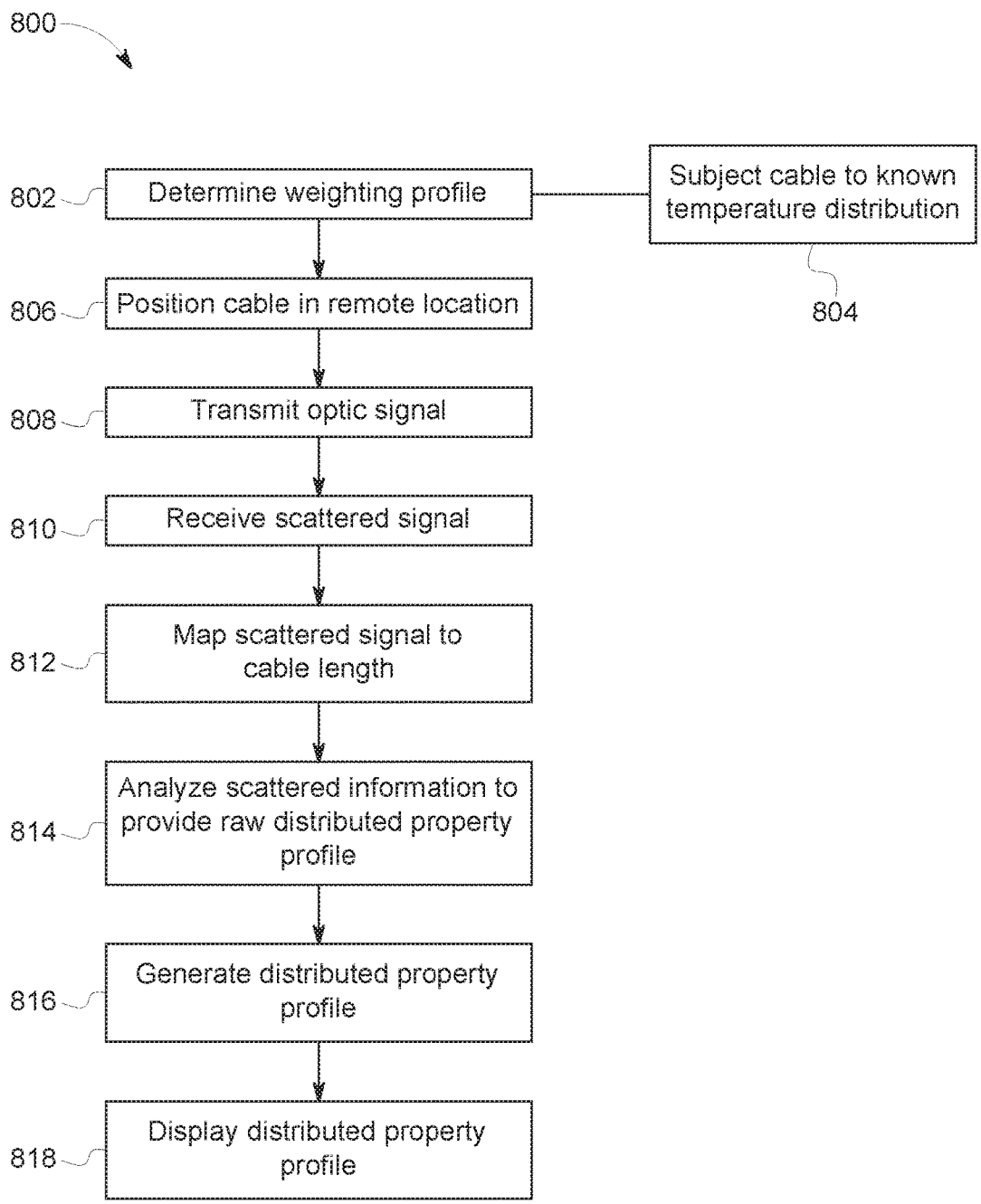
FIG. 8 is a flowchart of a method for determining a property distributed along a length of cable in accordance with various embodiments.

FIG. 8 provides a flowchart of a method 800 for determining a property distribution (e.g., temperature, pressure, strain) at points or locations distributed along a length of a cable. In various embodiments, the method 800, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 800 may be able to be used as one or more algorithms to direct hardware to perform operations described herein (e.g., instructions stored on memory 138 may be used to direct the processing unit 130 to perform one or more aspects of the method 800).

At 802, a weighting profile is determined. The weighting profile corresponds to the distribution of light of a pulse sent along a cable by a light source. The particular shape or properties of the profile are determined by characteristics of the cable and the light source. The weighting profile may be determined empirically or experimentally. For example, in the illustrated embodiment, at 804, the cable is subjected to a known temperature distribution. Then, a measured temperature profile is compared to the known temperature distribution and used to determine a weighting profile. For example, a variety of shapes (e.g., triangular and/or Gaussian) may be used, with the best fit being selected as the one with the least error between measured temperature and true temperature and, as the weighting profile to be used for a particular light source/cable combination. As discussed herein, the weighting function may be variable along the length of the cable, for example broadening along the length of the cable to account for dispersion.

At 806, the cable is positioned in a remote location, for which measurement of a given property (e.g., temperature, pressure, strain) at various locations (e.g., locations along the length of the cable) is desired to be determined.

At 808, an optical signal is transmitted. For example, the optical signal may be transmitted with a laser, and may be transmitted at a pulse wavelength and at a pulse duration and repetition rate. The pulse duration may correspond to a length of light beam that travels along the length of the cable. In some embodiments, for example, the optical signal may be transmitted at a pulse duration that corresponds to a 50 centimeter length of light traveling down the cable.

At 810, a scattered signal is received from the cable. The scattered signal may be received using one or more detectors (e.g., one or more photodetectors). The scattered signal, for example, may be a backscattered signal. The backscattered signal includes backscattered light at one or more wavelengths generated in response to the transmission of the optical signal or pulse transmitted at 808. One or more wavelengths of the backscattered signal may be selectively acquired and analyzed to determine an original or raw property profile. For example, backscattered light at the pulse wavelength may be acquired and analyzed as part of an analysis of Rayleigh scattering. As other examples, information from one wavelength that is longer than the pulse wavelength and one wavelength that is shorter than the pulse wavelength may be acquired and analyzed as part of Raman or Brillouin analyses. The backscattered signal may be acquired at a sampling rate. The sampling rate may be faster such that the pulse is sampled multiple times during its duration, i.e., corresponding to a shorter sampling length than the pulse length. For example, with a pulse duration corresponding to a 50 centimeter long pulse, the sampling rate may correspond to 12.5 centimeter lengths of the cable.

At 812, information from the scattered signal is mapped to the cable length. The particular location at which a given portion of the backscattered information is mapped to the cable length may be determined based on the time of sending the pulse, the time of receiving or sampling the portion of the backscattered information, and the speed of light through the cable.

At 814 of the depicted embodiment, the acquired scattered information is analyzed to provide a raw distributed property profile. The scattered information is mapped in the illustrated embodiment as a measured quantity along the length of cable. For example, in some embodiments, the raw distributed property profile may be generated using a conventional Raman analysis to provide a raw temperature profile. As other examples, Rayleigh or Brilloun analyses may be utilized to provide a raw distributed property profile.

At 816, a distributed property profile is generated. The distributed property profile is defined along the length of the cable, and is generated using the weighting profile. For example, the weighting profile may be used to de-convolve a spatial averaging effect from the raw distributed property profile corresponding to the scattered signal. As discussed herein, in some embodiments, a weighting profile (e.g., a Guassian profile) may be constructed using a higher resolution interval than the interval corresponding to the sampling rate, and used to de-convolve a cubic spline fit curve having a similar higher resolution than data acquired at the sampling rate.

At 818, the distributed property profile is displayed. The display may be part of print out, and/or may be displayed on a screen (e.g., using input/output unit 136).

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optic drive, and the like, including storage and processing at another facility such as cloud storage and computing. The storage device may also be other similar means for loading computer programs or other instructions into the computer or processor.

As used herein, the term "computer," "controller," and "module" may each include any processor-based or microprocessor-based system including systems using microcontrollers, reduced instruction set computers (RISC), application specific integrated circuits (ASICs), logic circuits, GPUs, FPGAs, and any other circuit or processor capable of executing the functions described herein. The above examples are exemplary only, and are thus not intended to limit in any way the definition and/or meaning of the term "module" or "computer."

The computer, module, or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, module, or processor as a processing machine to perform specific operations such as the methods and processes of the various embodiments described and/or illustrated herein. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program. The individual components of the various embodiments may be virtualized and hosted by a cloud type computational environment, for example to allow for dynamic allocation of computational power, without requiring the user concerning the location, configuration, and/or specific hardware of the computer system.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, and also to enable a person having ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A time domain distributed measurement system comprising:
   a cable having a length;
   a light source operably coupled to the cable and configured to transmit an optical signal to the cable;
   at least one detector operably coupled to the cable; and
   at least one processor operably coupled to the at least one detector and configured to:
      receive a scattered signal via the at least one detector from the cable responsive to the optical signal transmitted to the cable;
      map the scattered signal to the length of the cable; and
      de-convolve a spatial averaging effect of the scattered signal using a weighting profile, wherein the weighting profile is determined based on a combination of the light source and the cable to generate a distributed property profile defined along the length of the cable.

2. The measurement system of claim 1, wherein the light source transmits the optical signal at a pulse duration, and the at least one processor acquires the scattered signal at a sampling rate, wherein the sampling rate is faster than the pulse duration.

3. The measurement system of claim 2, wherein the weighting profile is at a higher spatial resolution than a resolution determined by the sampling rate, wherein the at least one processor is configured to interpolate the scattered signal to provide increased resolution for de-convolving the spatial averaging effect.

4. The measurement system of claim 2, wherein the at least one processor is configured to control the light source and the at least one detector to synchronize acquisition of the scattered signal by the at least one detector with transmission of the optical signal.

5. The measurement system of claim 1, wherein the light source transmits the optical signal at a pulse wavelength, and wherein the at least one processor acquires the scattered signal at the pulse wavelength.

6. The measurement system of claim 1, wherein the light source transmits the optical signal at a pulse wavelength, and wherein the at least one processor acquires the scattered signal at least two wavelengths that are different from the pulse wavelength.

7. The measurement system of claim 1, wherein the at least one processor is configured to analyze Raman scattering to determine a distributed temperature profile.

8. The measurement system of claim 1, wherein the weighting profile has a Gaussian shape.

9. A method comprising:
   transmitting, with a light source operably coupled to a cable, an optical signal to the cable;
   receiving, with at least one processor operably coupled to the cable, a scattered signal from the cable responsive to the optical signal transmitted to the cable;
   mapping the scattered signal to the length of the cable; and
   generating a distributed property profile defined along the length of the cable by de-convolving a spatial averaging effect of the scattered signal using a weighting profile, wherein the weighting profile is determined based on a combination of the light source and the cable.

10. The method of claim 9, further comprising subjecting the cable to a known temperature distribution, and determining the weighting profile based on the known temperature distribution.

11. The method of claim 9, further comprising transmitting the optical signal at a pulse duration, and acquiring the scattered signal at a sampling rate, wherein the sampling rate is faster than the pulse duration.

12. The method of claim 11, wherein the weighting profile is at a higher spatial resolution than a resolution determined by the sampling rate, the method further comprising interpolating the scattered signal to provide increased resolution for de-convolving the spatial averaging effect.

13. The method of claim 11, further comprising controlling the light source and at least one detector to synchronize acquisition of the scattered signal with transmission of the optical signal.

14. The method of claim 9, further comprising transmitting the optical signal at a pulse wavelength, and acquiring the scattered signal at the pulse wavelength.

15. The method of claim 9, further comprising transmitting the optical signal at a pulse wavelength, and acquiring the scattered signal at least two wavelengths that are different from the pulse wavelength.

16. The method of claim 9, further comprising analyzing Raman scattering to determine a distributed temperature profile.

17. The method of claim 9, wherein the weighting profile has a Gaussian shape.

18. A tangible and non-transitory computer readable medium comprising one or more computer software modules configured to direct one or more processors to:
transmit an optical signal to the cable;
receive a scattered signal from the cable responsive to the optical signal transmitted to the cable;
map the scattered signal to the length of the cable; and
generate a distributed property profile defined along the length of the cable by de-convolving a spatial averaging effect of the scattered signal using a weighting profile, wherein the weighting profile is determined based on a combination of the light source and the cable.

19. The tangible and non-transitory computer readable medium of claim 18, wherein the computer readable medium is further configured to transmit the optical signal at a pulse duration, and to acquire the scattered signal at a sampling rate, wherein the sampling rate is faster than the pulse duration.

20. The tangible and non-transitory computer readable medium of claim 18, wherein the computer readable medium is further configured to generate a distributed temperature profile along the length of the cable.

21. The measurement system of claim 1, wherein the weighting profile varies along the length of the cable.

22. The measurement system of claim 1, wherein the weighting profile has a triangular shape.

23. The measurement system of claim 8, wherein the Gaussian shape comprises a first Gaussian profile having a Sigma of 7 centimeters or a second Gaussian profile having a Sigma of 10 centimeters.

* * * * *